(12) United States Patent
Wang et al.

(10) Patent No.: US 8,445,025 B2
(45) Date of Patent: May 21, 2013

(54) HYBRID SUPERPARAMAGNETIC IRON OXIDE NANOPARTICLES AND POLYETHYLENIMINE AS A MAGNETOPLEX FOR GENE TRANSFECTION

(75) Inventors: Li-Fang Wang, Kaohsiung (TW); Shuo-Li Sun, Kaohsiung (TW); Yu-Lun Lo, Nantou County (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 13/074,491

(22) Filed: Mar. 29, 2011

(65) Prior Publication Data
US 2012/0157626 A1 Jun. 21, 2012

(30) Foreign Application Priority Data

Dec. 20, 2010 (TW) ................................ 99144853 A

(51) Int. Cl.
*A61K 9/50* (2006.01)
(52) U.S. Cl.
USPC ........... 424/497; 424/489; 424/490; 424/501; 424/646; 524/275; 524/284; 524/301; 524/435; 525/540; 525/186; 525/360; 525/370; 525/372; 977/783; 977/811; 977/904; 977/915; 977/916

(58) Field of Classification Search
USPC .......... 424/489, 490, 497, 501, 646; 524/275, 524/284, 301, 435; 525/540, 186, 360, 370, 525/372; 977/783, 811, 904, 915, 916
See application file for complete search history.

(56) References Cited

U.S. PATENT DOCUMENTS

| 6,767,635 B1 * | 7/2004 | Bahr et al. ..................... 428/402 |
| 6,846,809 B2 | 1/2005 | Cristiano et al. |
| 2008/0075701 A1 | 3/2008 | Hong et al. |

OTHER PUBLICATIONS

Krotz, F., et al.; Journal of Vascular Research, 2003, vol. 40, p. 425-434.*
Ma, Y.H., et al.; Biomaterials, 2009, vol. 30, p. 3343-3351.*
Oz Biosciences, CombiMag Material Safety Data Sheet, 2007, p. 1-3.*
Briley-Saebo et al., "Hepatic Cellular Distribution and Degradation of Iron Oxide Nanoparticles Following Single Intravenous Injection in Rats: Implications for Magnetic Resonance Immaging," *Cell and Tissue Research*, vol. 316, 2004, pp. 315-323.
Chorny et al., "Magnetically Driven Plasmid DNA Delivery with Biodegradable Polymeric Nanoparticles," *The FASEB Journal*, vol. 21, Aug. 2007, pp. 2510-2519.
Namgung et al., "Hybrid Superparamagnetic Iron Oxide Nanoparticle-Branched Polyethylenimine Magnetoplexes for Gene Transfection of Vascular Endothelial Cells," *Biomaterials*, vol. 31, 2010, pp. 4204-4213.
U.S. Appl. No. 12/694,599, filed Jan. 27, 2010.
Office Action for Taiwanese Application No. 099144853 dated Nov. 27, 2012
*Preparation of Highly Water-Soluble and Specifically Tumor-Targeting Fe3O4 Nanoparticles*, Theses, 2009, Abstract; page 17 of Introduction.

* cited by examiner

*Primary Examiner* — Robert Jones, Jr.
(74) *Attorney, Agent, or Firm* — Alston & Bird LLP

(57) ABSTRACT

Disclosed are the nanoparticle and the method for the same, and the preparing method includes steps of mixing polyethylenimine (PEI) with the poly(acrylic acid)-bound iron oxide (PAAIO) to form a PEI-PAAIO polyelectrolyte complex (PEC) and mixing the PEI-PAAIO PEC with genetic material such as plasmid DNA to form the PEI-PAAIO/pDNA magnetic nanoparticle. The PEI-PAAIO/pDNA magnetoplex is highly water dispersible and suitable for long term storage, shows superparamagnetism, low cytotoxicity, high stability and nice transfection efficiency, and thus the PEI-PAAIO PEC can replace PEI as a non-viral gene vector.

4 Claims, 11 Drawing Sheets

HYBRID SUPERPARAMAGNETIC IRON OXIDE NANOPARTICLES AND POLYETHYLENIMINE AS A MAGNETOPLEX FOR GENE TRANSFECTION

CROSS-REFERENCE TO RELATED APPLICATION AND CLAIM OF PRIORITY

The application claims the benefit of Taiwan Patent Application No. 099144853, filed on Dec. 20, 2010, in the Taiwan Intellectual Property Office, the disclosures of which are incorporated herein in their entirety by reference.

FIELD OF THE INVENTION

The present invention relates to nanoparticles. In particular, the present invention relates to the nanoparticles made with hybrid superparamagnetic iron oxide and polyethylenimine. The genetic materials carried by the nanoparticles can be transfected into cells, and such nanoparticles can be applied in clinic medicine.

BACKGROUND OF THE INVENTION

Transfection or transformation is referred to the technology for transporting the genetic materials into cells or organisms. For instance, an electric field is performed on the plasmid DNA, and the plasmid DNA then is transported into cells to express its biological functions or to be translated as specific proteins. Alternatively, liposome with positive charge is mixed with negative charge DNA to form complex, and DNA is delivered to cytoplasm by the fusion of the complex with cell membrane or endocytosis.

U.S. Pat. No. 6,846,809 discloses a DNA vector for DNA delivery, wherein nucleic acid and polycation are mixed to form a liquid transfection composition, which directly contacts with cancer cells or tissues having cancer cells, so that nucleic acid is delivered to cancer cells to inhibit their growth. However, since no external electric field or magnetic field is performed on the liquid transfection composition, the transfection efficiency is not high.

In recent years, the magnetic transfection technology is developed, which integrates the genetic materials such as DNA, small interfering RNA (siRNA) and so on with magnetic nanoparticles to transport the genetic materials using a magnetic field. For instance, US Patent Publication No. 2008/0075701 discloses a composition for magnetofection, which envelopes the magnetic nanoparticles (MNPs) and the genetic materials inside the hydrophilic vector (liposome) to form the spherical vehicle. At first, the MNPs are coated with surfactant (organic acid), and the excess surfactant is removed with ultrasonication. The MNPs then are enveloped inside the liposome, but surfactant is not enveloped thereinside. Subsequently, the genetic materials are added to the fluid containing liposome-enveloped MNPs, and the genetic materials pass into the liposome via the lipid bilayer structure to form the end product, the spherical vehicle. However, the processing steps of the MNPs in US 2008/0075701 are too complicated, and the genetic materials need to pass through the lipid bilayer structure to be enveloped with the liposome. Thus, it will reduce the probability that the nanoparticles and magnetic materials are enveloped inside the liposome at the same time.

The MNP based on iron oxide nanoparticles can be degraded in physiological conditions over a time period of a month suspiciously corresponding to ferritin synthesis (Briley-Saebo et al., 2004). Since the internalized iron oxide nanoparticles are biotransformed, thus, there would be no safety concern using MNPs as a drug delivery system.

SUMMARY OF THE INVENTION

For overcoming the safety problem of the MNPs in the current technologies, the MNPs (or named magnetoplexes) of the present invention are highly water dispensable and can be longtime reserved, and have properties of superparamagnetism, low cytotoxicity, high stability and excellent transfection efficiency. The MNPs can replace polyethylenimine (PEI) to be the non-viral gene vector.

The present invention provides a method for preparing a nanoparticle, including steps of: reacting a PEI with a polyacrylic acid-bound iron oxide (PAAIO) to obtain a polyelectrolyte complex (PEC); and encapsulating (or incorporating) a genetic material with the PEC to form the nanoparticle. The above preparation method of the present invention is simple and efficient with a high yield.

The present invention further provides a nanoparticle afforded by the aforementioned preparation method, and the nanoparticle includes: the PEC containing the PEI and the PAAIO configured on the PEI; and a genetic material coupled to the PEI.

The present invention further provides a nanoparticle, including: a PEC containing a positive charge molecule and a magnetic particle configured on the positive charge molecule; and a genetic material coupled to the positive charge molecule.

The positive charge molecule includes but not limit to PEI, and PEGlayted PEI also can be applicable in the present invention. The PEGlayed PEI is referred to that polyethylene glycol (PEG) polymer chains are covalently attached to the PEI. The magnetic particle includes but not limit to metal particles. The metal particles include but not limit to gold nanoparticles, silver nanoparticles and iron nanoparticles, and the genetic material can be DNA, RNA, complementary DNA, small interfering RNA (siRNA), micro RNA and so on.

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

The present invention will now be described more specifically with reference to the following Embodiments. It is to be noted that the following descriptions of preferred Embodiments of this invention are presented herein for purpose of illustration and description only; it is not intended to be exhaustive or to be limited to the precise form disclosed.

The magnetic nanoparticle (MNP) of the present invention includes metal oxide, carboxylic molecules, positive charge molecules, and genetic materials. The genetic materials include but not limit to the nucleic acid molecule such as DNA, RNA, complementary DNA (cDNA), small interfering RNA (siRNA), micro RNA and so on. The metal oxide can be bound with an acidic molecule, and the genetic material is electrostatically coupled to the positive charge molecule. In the present invention, PEI and PEGlayted PEI can be used as the positive charge molecule, in which PEGlayed PEI is referred to that polyethylene glycol (PEG) polymer chains are covalently attached to the PEI.

Figure 1:
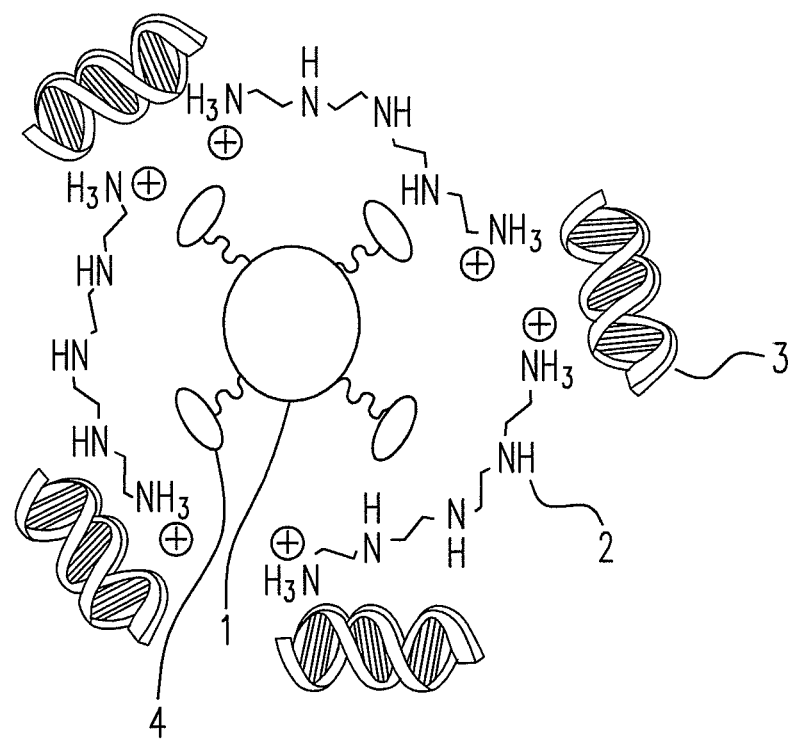
FIG. 1 schematically depicts a diagram showing the PEI-PAAIO/pDNA magnetoplex of the present invention.

Please refer to FIG. 1, which schematically depicts a diagram showing the PEI-PAAIO/pDNA magnetic nanoparticle (or magnetoplex) of the present invention. PEI-PAAIO/pDNA magnetoplex includes iron oxide 1, polyethylenimine (PEI) 2 and plasmid DNA (abbreviated as pPDA) 3. Poly(acrylic acid) (PAA) 4 is bound with $Fe_3O_4$ 1 to form the PAA-bound iron oxide (PAAIO), which is obtained via a one-step reaction of $Fe_3O_4$ coated with PAA 4. The negative charge pDNA 3 is electrically coupled to the positive charge PEI 2 to form the PEI-PAAIO/pDNA magnetoplex. The PEI-PAAIO/pDNA magnetoplex formed by coupling PEI and PAAIO can be the non-viral gene vector. The metal particle being the core of PEI-PAAIO/pDNA magnetoplex is water soluble, and include but not limit to gold nanoparticle, silver nanoparticle and iron nanoparticle.

EXPERIMENTS

1. Major Reagents

Iron(III) chloride, anhydrous ($FeCl_3$), and poly(acrylic acid) (PAA, Mw 2,000 g/mol) were obtained from TCI (Tokyo, Japan). Polyethylenimine (PEI, branched, Mw 25,000 g/mol) was acquired from Polyscience (Warrington, Pa., USA). Potassium hexacyanoferrate (II) trihydrate was purchased from Showa (Tokyo, Japan). The reporter gene pEGFP-C1 was purchased from Clontech (Palo Alto, Calif., USA) and pGL3-control and its luciferase assay kit with reporter lysis buffer was purchased from Promega (Madison, Wis., USA). The aforementioned plasmid DNAs (pDNA), pEGFP-C1 and pGL3-control, were propagated in a chemically competent *Escherichia coli* stain DH5α (GibcoBRL, Gaitherbury, Md., USA), and purified by Viogene Plasmids Maxi kit (Viogene, Sunnyvale, Calif., USA).

2. Synthesis of PAAIO and PEI Coated PAAIO (PEI-PAAIO)

PAAIO was synthesized via a one-step reaction of $Fe_3O_4$ coated with PAA according to U.S. patent application Ser. No. 12/694,599. PEI coated PAAIO (PEI-PAAIO) was prepared by mixing PEI and PAAIO at a stock concentration of 1 mg/mL in double deionized (DD) water. The total volume of 15 mL of PEI and PAAIO prepared at two weight ratios of 1/1 or 1/2 was used for hydrodynamic particle size and zeta potential tests. The PEI-PAAIO nanoparticles were ultrasonicated for 5 minutes. The unbound PEI was removed by placing a permanent magnet (Nd—Fe—B of 6000 Gauss (G)) near the test tube and the supernatant solution was carefully withdrawn. The magnetic-attracted PEI-PAAIO nanoparticles were resuspended in 15 mL DD water and centrifuged at 6000 rpm for 5 minutes, and the supernatant was combined with the previously withdrawn supernatant for the concentration measurement of unbound PEI. The precipitate was resuspended with 15 mL DD water as a stock solution for further uses.

3. Characterization of PEI-PAAIO

The evidence of successful PEI coating on PAAIO surface was confirmed by Fourier transform infrared (FTIR). FTIR spectra were performed using a Perkin-Elmer system 2000 spectrometer. Dried samples were ground with potassium bromide (KBr) powder and pressed into pellets for FTIR measurements. Sixty-four scans were signal-averaged in the range from 4000 to 400 $cm^{-1}$ at a resolution of 4 $cm^{-1}$. Electron spectroscopy for chemical analysis (ESCA) measurements was performed on a ST PHI 5000 Versa Probe (Sliedrecht, Netherlands) spectrometer using a monochromated Al Kα X-ray source. The relative atomic concentration of each element at the sample surface was calculated from the peak area using the atomic sensitivity factor. Spectra were recorded over a range of binding energies from 0 to 800 eV with a pass energy of 100 eV for the wide scan survey and a pass energy of 20 eV for high energy resolution spectra for regions of $N_{1s}$. The magnetic properties were measured using a magnetic properties measurement system (MPMS) from Quantum Design (MPMS-XL 7), which utilizes a superconducting quantum interference device (SQUID) magnetometer at fields ranging from −15 to 15 K Oe at 25° C.

4. Preparation and Characterization of PEI-PAAIO/pDNA Magnetoplexes

Since the pDNA concentration in magnetoplexes was fixed, manipulating the PEI-PAAIO concentration could be used to adjust the nanoparticle/pDNA (N/P) ratios between non-viral gene vectors and the plasmid DNA. Equal volumes of the PEI-PAAIO and the pDNA solutions were mixed at N/P ratios from 1 to 30 and immediately vortexed at high speed for 60 seconds. The PEI-PAAIO/pDNA magnetoplexes were kept at room temperature for 30 minutes for complete complexation before analysis.

DNA binding. DNA binding ability of magnetoplexes was evaluated by agarose gel electrophoresis. The magnetoplexes were prepared at various N/P ratios using the procedure stated above. After 0.5 hour or 4 hours standing with or without 10% fetal bovine serum (FBS), the stability of the magnetoplexes was performed by gel electrophoresis with 0.8% agarose.

Dynamic light scattering (DLS) and zeta potential. The averaged hydrodynamic diameter and zeta potential of PAAIO, PEI-PAAIO and PEI-PAAIO/pDNA were measured by laser Doppler anemometry using a Zetasizer Nano ZS instrument (Marlvern, Worcestershire, UK). Light scattering measurements were carried out with a laser at 633 nm with a 90° scattering angle. The concentration of the sample was 0.1 mg/mL and the temperature was maintained at 25° C. Polystyrene nanospheres (220±6 nm and −50 mV; Duke Scientific, USA) were used to verify the performance of the instrument. The particle size and zeta potential of each sample was performed in triplicate.

Transmission electron microscopy (TEM). The size and morphology of magnetoplexes were visualized by cryo-TEM (Jeol JEM-1200, Tokyo, Japan). A carbon coated 200 mesh copper specimen grid (Agar Scientific Ltd. Essex, UK) was glow-discharged for 1.5 minutes. One drop of the sample solution was deposited on the grid and left to air-dry at room temperature, and was then examined with an electron microscope.

5. Cytotoxicity Assay

HEK 293T cells (human embryonic kidney 293T cell line) were seeded in 12-well tissue culture plates at a density of $1 \times 10^5$ cells per well in Dulbecco's Modified Eagles' Medium (DMEM) containing 10% FBS for 24 hours. Cytotoxicity of PEI-PAAIO (or PEI-PAAIO/pDNA magnetoplexes) was evaluated by determining the cell viability after 4 hours incubation in a serum-free DMEM followed by 72 hours post incubation in the DMEM containing 10% FBS at the same condition. In addition, the cytotoxicity of the nanoparticle or magnetoplex-treated cells was examined in the presence of an average 3000-G static magnetic field of Nd—Fe—B disk magnets underneath the cells during the 4 hours incubation period. The number of viable cells was determined by estimation of their mitochondrial reductase activity using the tetrazolium-based colorimetric method (MTT conversion test).

6. Transfection Efficiency

HEK 293T cells were seeded at a density of $1 \times 10^5$/well in 12 well plates and incubated in DMEM medium containing 10% FBS for 24 hours before transfection. When the cells were at 50% to 70% confluence, the culture medium was replaced with 1 mL of DMEM with or without 10% FBS. In addition, magnetoplexes with 4 µg pEGFP-C1 (control) and PEI-PAAIO/pDNA magnetoplex were prepared, and the medium was replaced with fresh complete-medium and the cells were incubated for 72 hours post transfection after pEGFP-C1 or PEI-PAAIO/pDNA magnetoplex was cultured with cells for 4 hour incubation with or without a static magnetic field. The green fluorescent protein (GFP) expression was directly visualized under a fluorescence microscope.

For the luciferase assay, the procedures as stated above were repeated to determine the transfection efficiency of the magnetoplexes compared with naked DNA (as a negative control) and PEI/pDNA polyplex at an N/P ratio of 10 (as a positive control) in HEK 293T cells and U87 (human glioblastoma cell line) cells. To quantify the luciferase expression, transfected cells were rinsed gently with 1 mL of 0.1 M PBS (phosphate buffered saline, twice), and then added to 200 µL/well of lysis buffer (0.1 M Tris-HCl, 2 mM ethylenediaminetetraacetic acid (EDTA), and 0.1% Triton X-100, pH 7.8) and let stand overnight at −20° C. Next day, each cell lysate was warmed to room temperature and centrifuged at high speed for 30 minutes. The luciferase activity was monitored using the TopCount NXT™ microplate scintillation and luminescence counter (Perkin Elmer, N.J., USA) after mixing the supernatant with the luciferase assay reagent (Promega, Madison, Wis., USA). The total protein content of the cell lysate was examined using a BCA protein assay kit (Pierce Rockford, Ill., USA).

7. Cellular Uptake

The internalized iron amount of PEI-PAAIO was quantified by inductively coupled plasma-optical emission spectrometer (ICP-OES, Optima 7000DV, Perkin Elmer, Boston, Mass., USA). The protein content of the half cell lysate was examined using the BCA protein assay kit, and the other half cell lysate was dissolved in 37% HCl and incubated at 70° C. for 1 hour. The samples were diluted to a final volume of 3 mL for analysis. The iron content of the samples were calculated based on an $Fe(NO_3)_3$ calibration curve.

The internalized PEI-PAAIO nanoparticles within HEK 293T cells was directly visualized by Prussian blue staining of iron. Prussian blue solution was prepared by mixing 10 mL of 2% potassium hexacyanoferrate (II) trihydrate solution and 5 mL of 2% HCl. The internalized $Fe^{3+}$ ions of PAAIO turn to bright blue pigment when reacted with the ferrocyanide ions. After 4 hours incubation with PEI-PAAIO as aforementioned, the cells were washed with 0.1M PBS (thrice) and fixed with 3.7% formaldehyde for 10 minutes, and washed again with PBS (thrice). Prussian blue solution of 1 mL/well was added and incubated with the cells for 30 minutes. Blue color can be visualized using an optical microscope.

8. Statistical Methods

Means, standard deviation (SD), and standard error (SE) of the data were calculated. Differences between the experimental groups and the control groups were tested using Student's-Newman-Keuls' test and $p<0.05$ was considered significant.

Results

1. Characterization of PEI-PAAIO

Figure 2A:
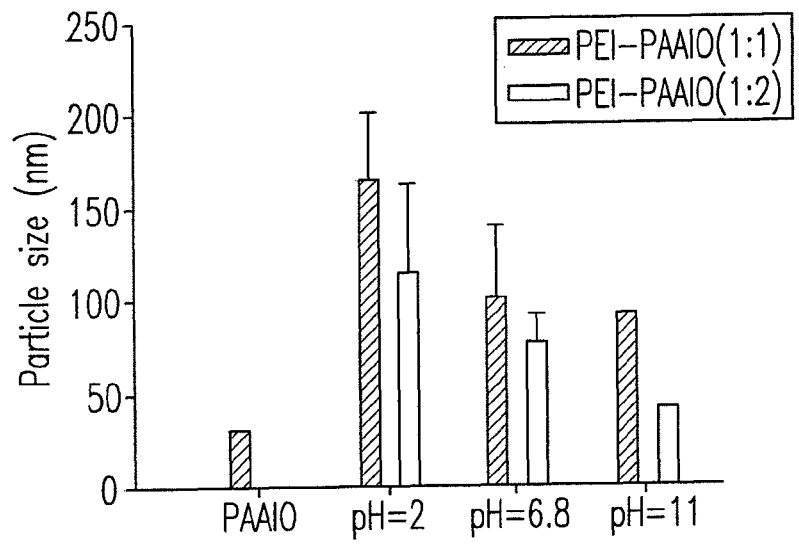
FIGS. 2(a) and 2(b) respectively illustrate the diagrams showing (a) hydrodynamic particle size and (b) zeta potential using two weight ratios between PAAIO and PEI in the preparations two PEI-PAAIO complexes.
Figure 2B:
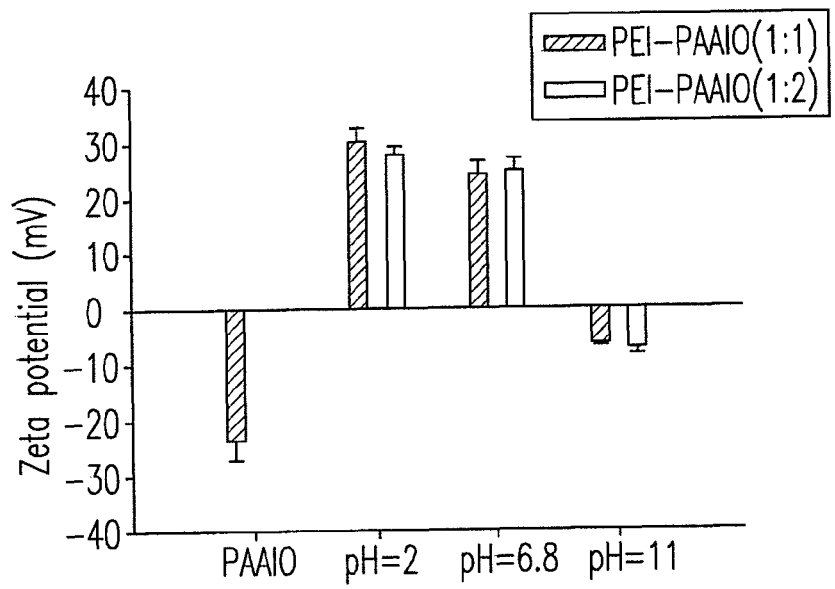
Figure 3A:
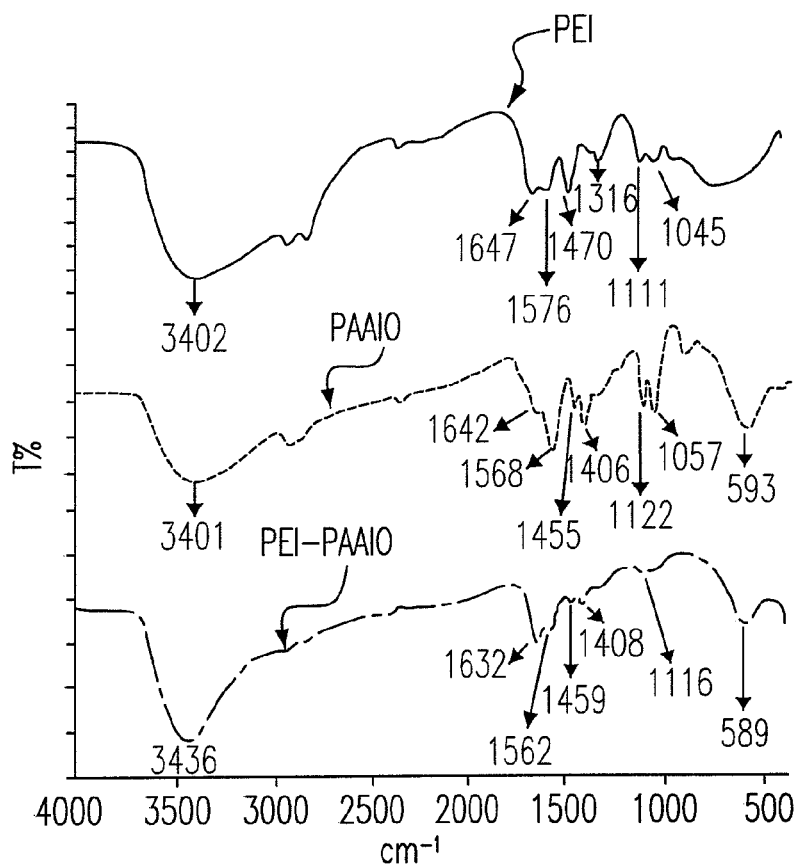
FIG. 3(a) illustrates the diagrams showing FTIR spectrum of PEI, PAAIO and PEI-PAAIO complexes.
Figure 3B:
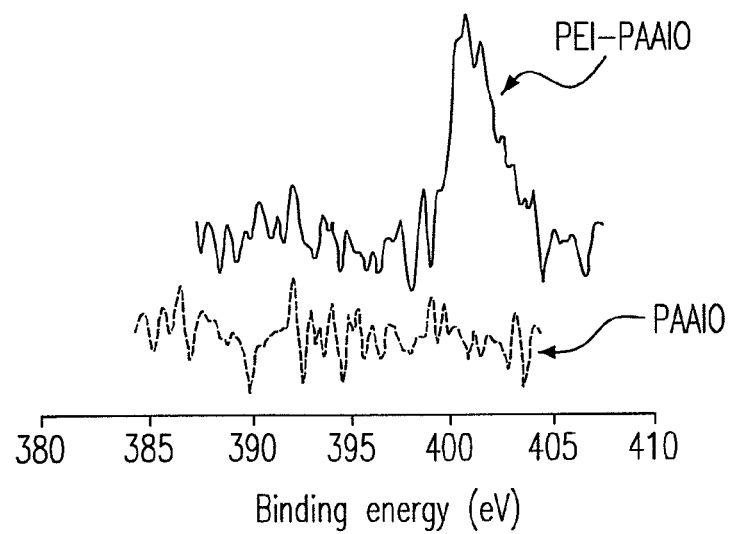
FIGS. 3(b) and 3(c) illustrates the diagrams showing ESCA spectra of (b) PAAIO and (c) PEI-PAAIO complexes.
Figure 3C:
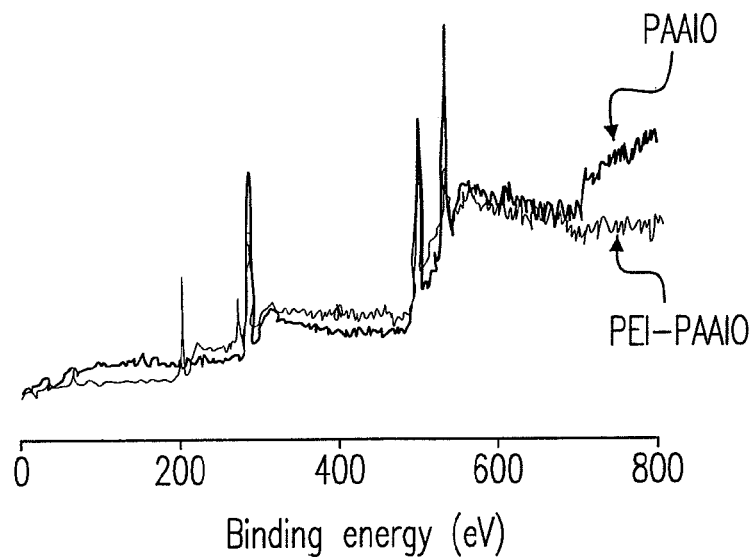
Figure 3D:
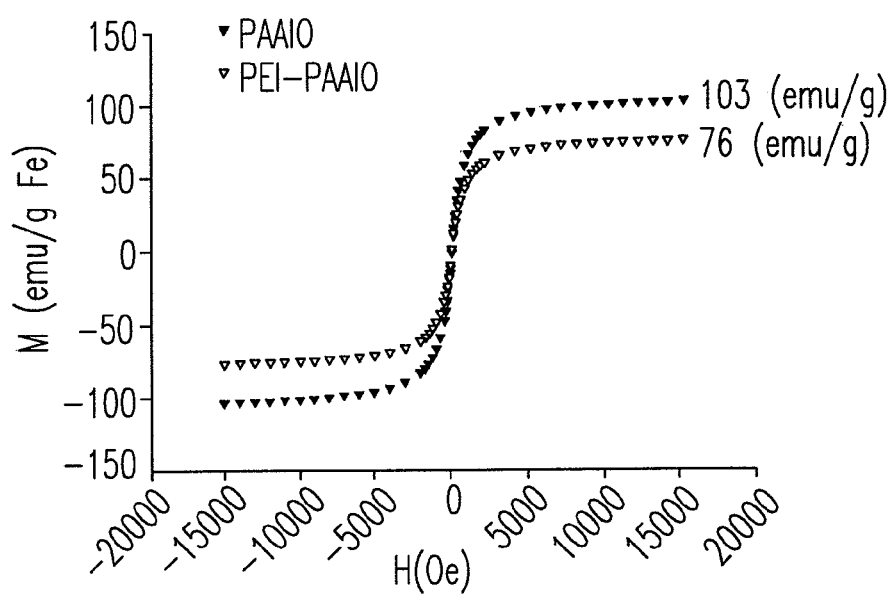
FIG. 3(d) illustrates the diagram showing SQUID magnetization curves as a function of field at 25° C. for PAAIO and PEI-PAAIO complexes.

Optimized conditions using various ratios between PEI and PAAIO to form a stable complex were tested using pH 2.0, 6.8 and 11. Two weight ratios between PAAIO and PEI at 1:1 and 2:1 were chosen for particle size and zeta potential measurements. PAAIO had an average hydrodynamic diameter of 35 nm (FIG. 2(a)) and a negative zeta potential of −25 mV (FIG. 2(b)). Please continuously refer to FIG. 2(b), at pH 6.8, both PEI-PAAIO complexes showed similar zeta potentials of +22 mV but the PEI-PAAIO complex (PEI:PAAIO=1:2) had smaller particle diameter. Thus, the PEI-PAAIO complex (PEI:PAAIO=1:2) was chosen for all latter experiments. The positive zeta potential of the complexes explains the successful decoration of PEI on PAAIO. Please refer to the FTIR spectra of FIG. 3(a), PAAIO showed three characteristic stretchings at 1568, 1455 and 1406 $cm^{-1}$ and PEI showed three characteristic stretchings at 1647, 1576 and 1470 $cm^{-1}$. The primary amine stretching of PEI at 1647 $cm^{-1}$ shifted to 1632 $cm^{-1}$ and the asymmetric carboxylate peak at 1568 $cm^{-1}$ shifted to 1562 $cm^{-1}$ due to the electrostatic interactions. Moreover, the peak intensity of carboxylate stretching of PAAIO at 1562 $cm^{-1}$ decreased because of a PAAIO surface blocking by PEI. The further evidence of PEI decorated on PAAIO was also observed by ESCA where the binding energies of atoms $C_{1s}$, $N_{1s}$ and $O_{1s}$ appear at 283, 400 and 530 Ev (FIGS. 3(b) and 3(c)). The atom percentage of N was undetectable in PAAIO but the value of 4.7% was measured in PEI-PAAIO complex. The saturation magnetization (Ms) value of PEI-PAAIO complex was 76 emu/g Fe and 103 emu/g Fe for PAAIO (FIG. 3(d)). The Ms decreased after PEI coated on PAAIO. PEI-PAAIO complex remained superparamagnetic at room temperature and showed negligible hysteresis.

The concentration of PEI in PEI-PAAIO was determined by measuring the cuprammonium complex formed between PEI and copper (II) at 630 nm using a UV-vis spectrophotometer (Namgung et al., 2010). The value of 0.135±0.03 mg/mL was obtained based on a calibration curve of PEI. When the molecular weights of PAAIO and PEI were 2232 g/mol and 25,000 g/mol respectively, the molar percent of PEI in PEI-PAAIO was 1.37 mol %. This value was utilized to calculate N/P ratios between PEI-PAAIO and pDNA. The theoretical PEI value in feed was 33 wt %. The theoretical molar ratio between the amino units in PEI and the carboxylate units in PAA was approximately 3 to 1 in feed. The 13.5 wt % of PEI could be correlative to the ratio of 1.25 to 1 between amino and carboxylate groups.

2. Characterization of PEI-PAAIO/pDNA Magnetoplexes

By changing PEI-PAAIO weight and keeping pDNA weight as a constant, various N/P ratios of PEI-PAAIO/pDNA magnetoplexes were prepared. The binding ability between PEI-PAAIO and pDNA was studied by agarose gel electrophoresis retardation assay. The result shows that the pDNA could be well encapsulated at an N/P ratio higher than 5, and a well protection of pDNA from FBS degradation was observed at an N/P ratio of higher than 15. Therefore, it was ensured that pDNA within PEI-PAAIO was not degraded with serum and the stability of pDNA was maintained, and 4 hours incubation condition was chosen for the latter transgene expression.

Figure 4A:
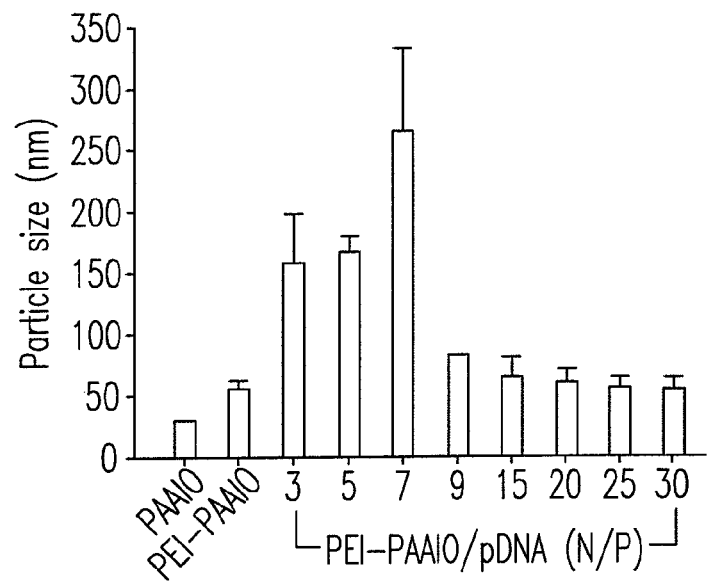
FIGS. 4(a) and 4(b) respectively illustrate the diagrams showing (a) particle size and (b) zeta potential of PEI-PAAIO/pDNA magnetoplex at various N/P ratios.
Figure 4B:
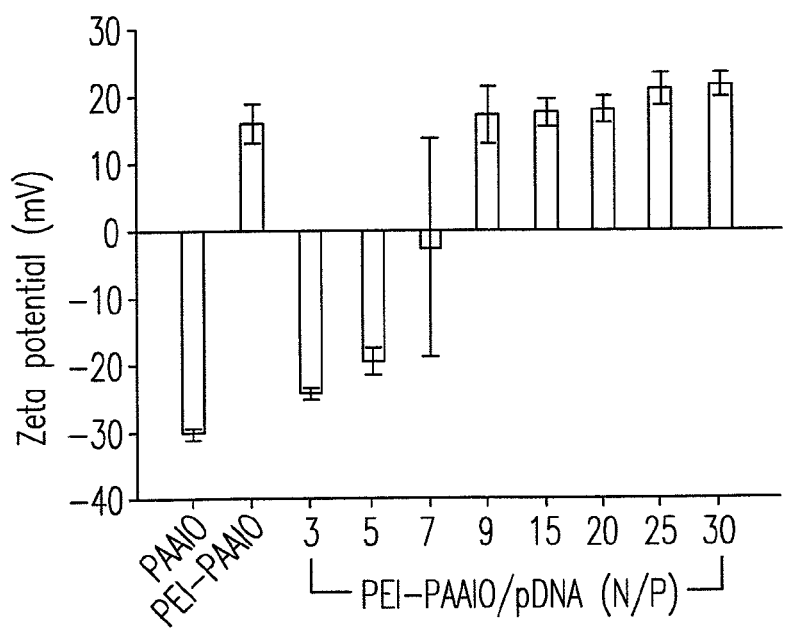

Please refer to FIG. 4(a), the hydrodynamic diameters of PAAIO and PEI-PAAIO were 30 nm and 50 nm measured by DLS. The particle average diameter of PEI-PAAIO/pDNA magnetoplexes increased to 150 nm at N/P ratios of 3 and 5, maximized at 7 (250 nm) and decreased dramatically to less than 100 nm when an N/P ratio was larger than 9. Please refer to FIG. 4(b), the surface charge of PAAIO is −30 mV and turns to a positive value of 16 mV following PEI decoration. This positive value of zeta potential also ascertains the successful coating of PEI onto PAAIO. The PEI-PAAIO/pDNA magnetoplexes formed from a low amount of PEI-PAAIO showed negative surface charges (at the N/P ratios of 3 and 5). The magnetoplex at the N/P ratio of 7 displayed a fluctuation of zeta potential between positive and negative values. The serious fluctuation in zeta potential may be attributed to a charge balance between positive PEI-PAAIO and negative pDNA at this N/P ratio. Increase in an N/P ratio of larger than 7 resulted in an increase in positive zeta potential of magnetoplexes.

The TEM morphological image of PAAIO shows an average particle diameter of 8.62±1.82 nm. The average particle diameter of PEI-PAAIO decorated by PEI slightly increased to 9.31±3.21 nm. All PEI-PAAIO/pDNA magnetoplexes at N/P ratios of 15, 20, and 30 appeared as clusters with evenly distributed bare iron oxide particles, and the measured cluster particle diameters were 103.6±16.5, 105.4±19.9, 128.8±14.4 and 95.8±11.2 nm in order. Larger sized MNP has been reported to exhibit higher transfection rates compared with small sized MNP (Chorny et al., 2007). Thus, the larger diameter of PEI-PAAIO/pDNA than that of the MNP may have the better magnetofection.

3. Cell Viability

Figure 5A:
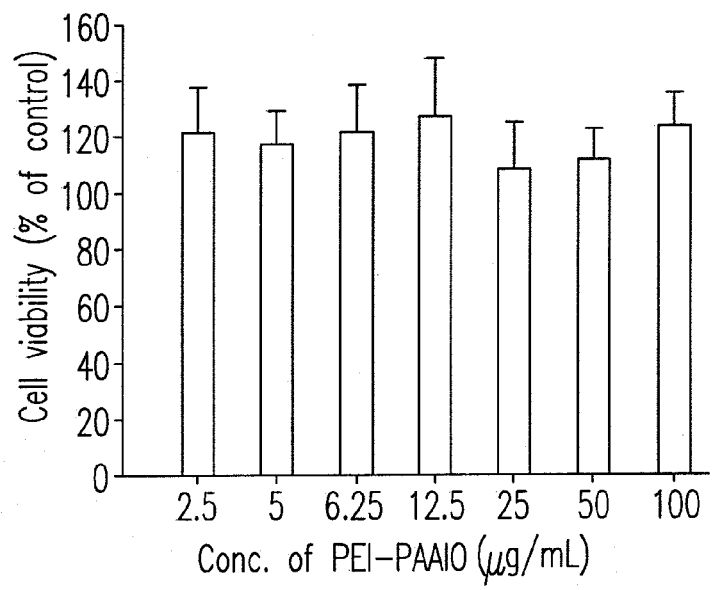
FIGS. 5(a) and 5(b) respectively illustrate the diagrams showing (a) cytotoxicity induced by PEI-PAAIO against HEK 293T cells at various concentration and (b) cytotoxicity induced by PEI-PAAIO/pDNA magnetoplexes at different N/P ratios with or without a magnetic field.
Figure 5B:
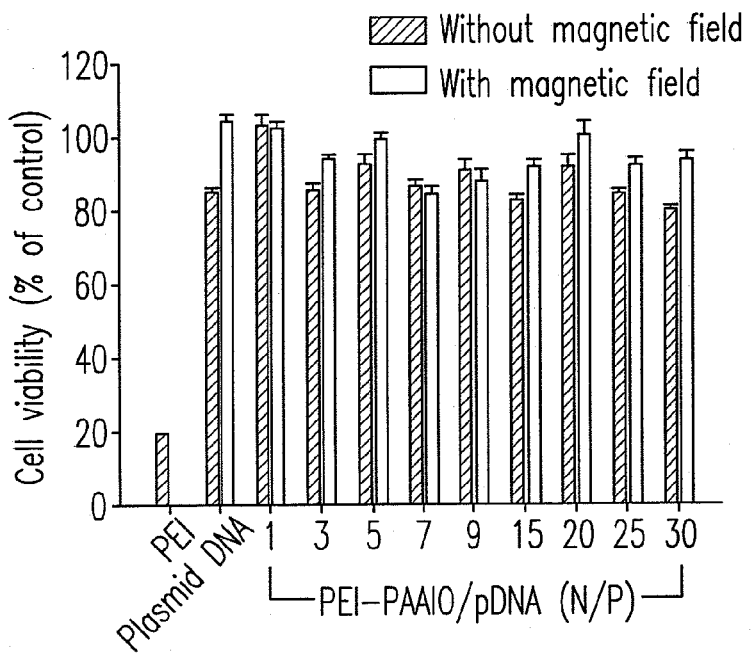

The cell viability of PEI-PAAIO was tested by MTT assay using HEK 293T cells as stated above. Please refer to FIG. 5(a), PEI-PAAIO exhibits no cytotoxicity in all tested concentrations. The high cell viability of PEI-PAAIO may be attributed to the low PEI content (The percentage of PEI was only 13.5 wt % in PEI-PAAIO). Please refer to FIG. 5(b), PEI-PAAIO/pDNA magnetoplexes with an N/P ratio ranging from 1 to 30 also showed minimal cytotoxicity. For instance, the PEI concentration in PEI-PAAIO at an N/P ratio of 30 was 16.2 µg/mL, where HEK 293T cells still remained 80% viable. The cytotoxicity of the PEI-PAAIO/pDNA magnetoplex at N/P ratio of 30 was dramatically less than PEI/pDNA polyplex prepared at an N/P ratio of 10. Thus, the PEI-PAAIO can be used as a non-viral gene vector superior to pure PEI if the cytotoxicity of gene vectors is a major concern. In addition, the external magnetic field applied underneath the cell culture plate does not influence the cell viability.

4. In vitro Gene Transfection

The aforementioned experiments have demonstrated that PEI-PAAIO endows the good condensation ability with pDNA and remains minimal cytotoxicity. As the experiment "6. Transfection efficiency" as above, two plasmid DNAs were used to test the transfection efficiency of PEI-PAAIO as a non-viral gene carrier, in which plasmids pEGFP-C1 and pGL3-control were chosen respectively for fluorescence and luminescence measurements.

Figure 6A:
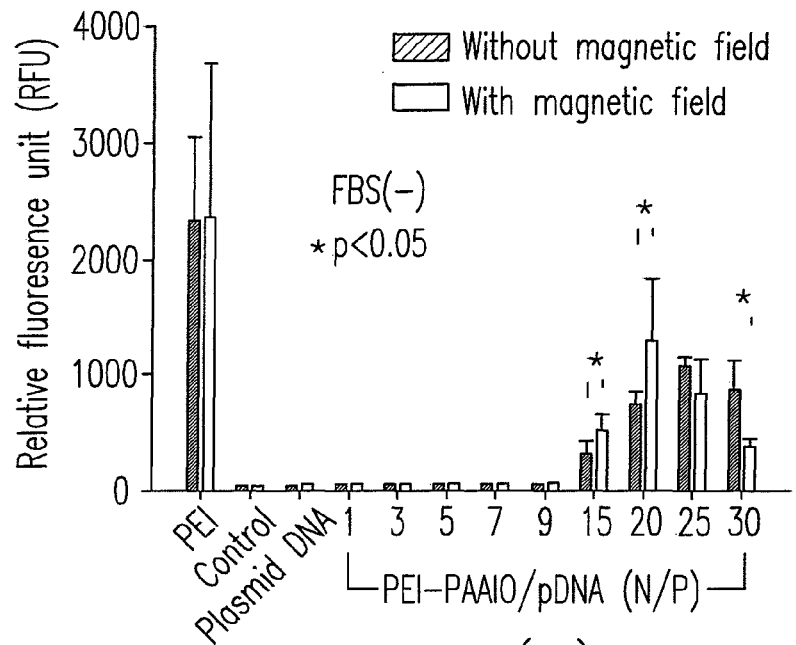
FIGS. 6(a) and 6(b) respectively illustrate the diagrams showing pEGFP-C1 expression in HEK 293T cells exposed to PEI-PAAIO/pDNA magnetoplexes (a) without 10% FBS and (b) with 10% FBS in the absence or presence of a magnetic field for 4 hours incubation followed by 72 hours post-incubation.
Figure 6B:
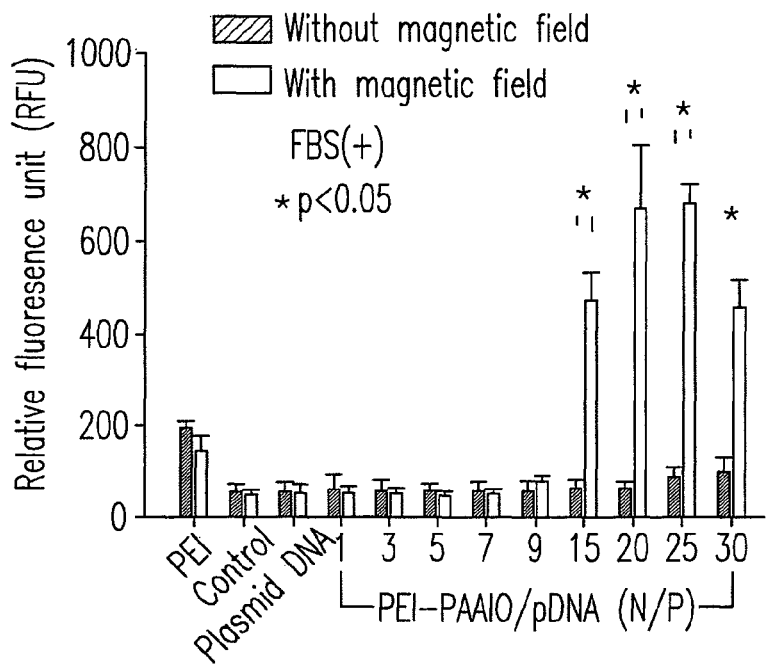

The relative green fluorescence expression from pEGFP-C1 was traced by fluorescence microscopy. FIG. 6(a) and FIG. 6(b) respectively showed the relative green fluorescence at the conditions without 10% FBS and with 10% FBS. Please refer to FIG. 6(a), the transfection efficiency increased with an increase in the N/P ratio between PEI-PAAIO and pEGFP-C1 and reached the maximum at the N/P ratio of 25. Upon applying a magnetic field, the transfection efficiency was improved at the N/P ratios of 15 and 20 but decreased at the ratios of 25 and 30. Please refer to FIG. 6(b), the green fluorescence intensity of PEI/pDNA reduced dramatically when 10% FBS was added to the cell culture medium. This may be due to the competition between FBS and pDNA with PEI, which reduces the pDNA concentration in the magnetoplexes. In addition, the FBS adsorption on PEI/pDNA surface has also been reported to inhibit transgene expression. Screening of transfection efficiencies under varied N/P ratios (PEI-PAAIO:pEGFP) without FBS revealed no magnetic enhancement of gene expression when the N/P ratio was less than 9. On contrast, a remarkable magnetic-enhanced effect was observed for the PEI-PAAIO/pEGFP magnetoplexes at the N/P ratio of larger than 15. This can be reasoned that the rapid internalization of the magnetoplexes with the high N/P ratios into the cells prevents pDNA destabilization from FBS interference during that incubation period.

Figure 7A:
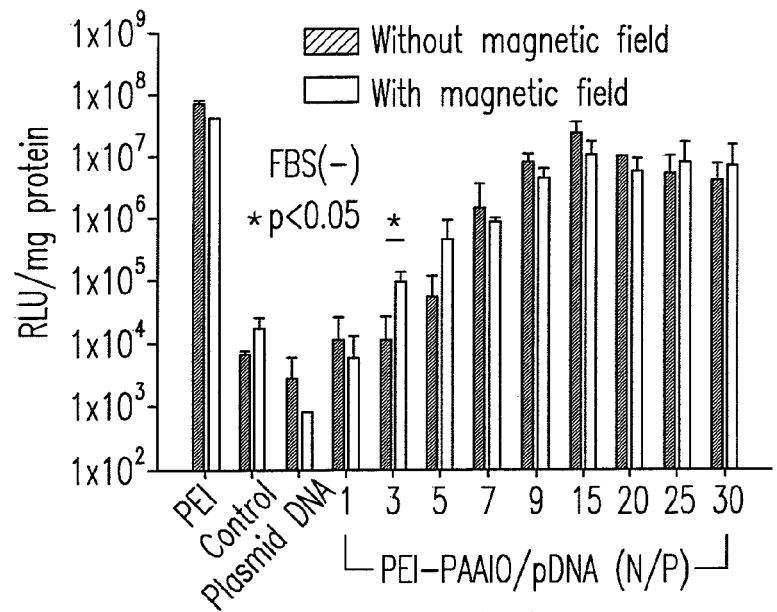
FIGS. 7(a) and 7(b) respectively illustrate the diagrams showing luciferase activity in HEK 293T cells exposed to PEI-PAAIO/pDNA magnetoplexes (a) without 10% FBS and (b) with 10% FBS in the absence or presence of a magnetic field for 4 hours incubation followed by 72 hours post-incubation.
Figure 7B:
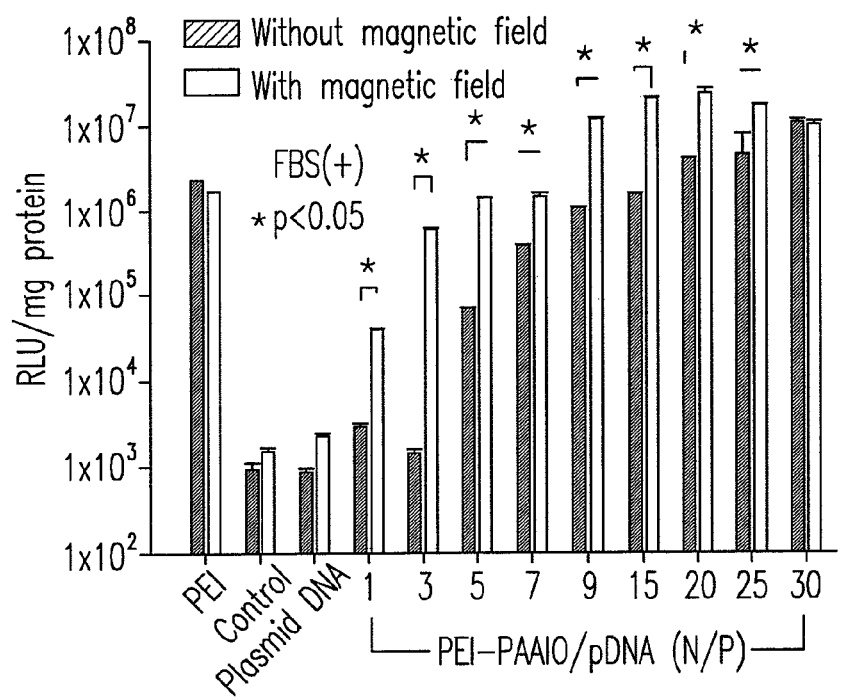

Next, a quantitative comparison of transfection ability of the magnetoplexes with the PEI-PAAIO polyplex with and without 10% FBS was also conducted by measuring luciferase gene expression using pGL3-control plasmid. Please refer to FIGS. 7(a) and 7(b), the consistent result revealed that in the presence or absence of FBS, a significantly improved transgene expression was obtained when a magnetic field was utilized to pull the PEI-PAAIO/pDNA magnetoplexes into the cells.

5. Cellular Uptake

The cellular uptake of PEI-PAAIO in HEK 293T cells was directly stained by Prussian blue. No discrete difference is shown with and without an imposed magnetic field in the absence of 10% FBS. Nevertheless, in the presence of 10% FBS, the blue color image becomes clearer with an increasing N/P ratio between PEI-PAAIO and pDNA under a magnetic field. It is demonstrated in the present invention that the larger particle diameters of PEI-PAAIO/pDNA magnetoplexes clearly demonstrated a higher cellular internalization when a magnetic field was applied.

Figure 8A:
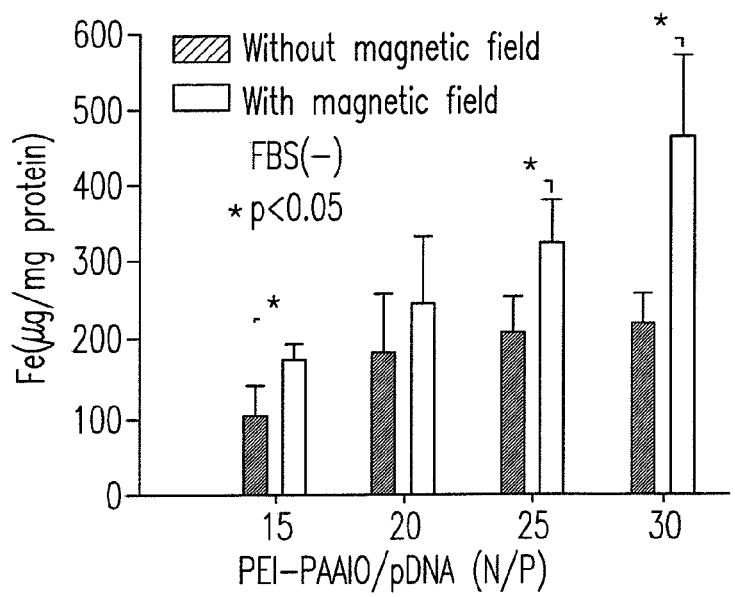
FIGS. 8(a) and 8(b) respectively illustrates the diagrams showing the HEK 293T cell-internalized iron oxides in PEI-PAAIO/pDNA magnetoplexes by ICP-OES (a) without 10% FBS and (b) with 10% FBS in the absence or presence of a magnetic field for 4 hours incubation.
Figure 8B:
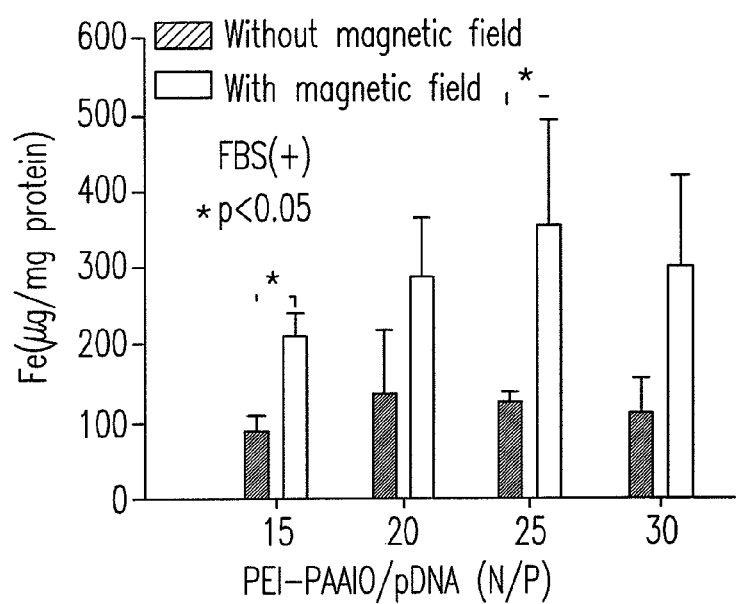

In addition, the quantity of iron normalized to total cell population was determined by ICP-OES. Please refer to FIGS. 8(a) and 8(b), which respectively illustrate the quantity of iron within cells (a) without 10% FBS and (b) with 10% FBS in the absence or presence of a magnetic field. The internalized iron amount within the cells showed no correlation with an increasing N/P ratio when a magnetic field was absent. On the contrary, the cellular uptake of iron oxide particles increased with an increasing N/P ratio under a magnetic field. Independent of FBS, the internalized iron oxide particles increased upon an imposed magnetic field. At an N/P ratio of 30, the internalized iron amount was approximately 2-fold if the magnetic field was applied. In summary, PEI-PAAIO/pDNA magnetoplexes is very efficient for gene tranfection in HEK 293T cells in a circumstances of FBS.

Figure 9A:
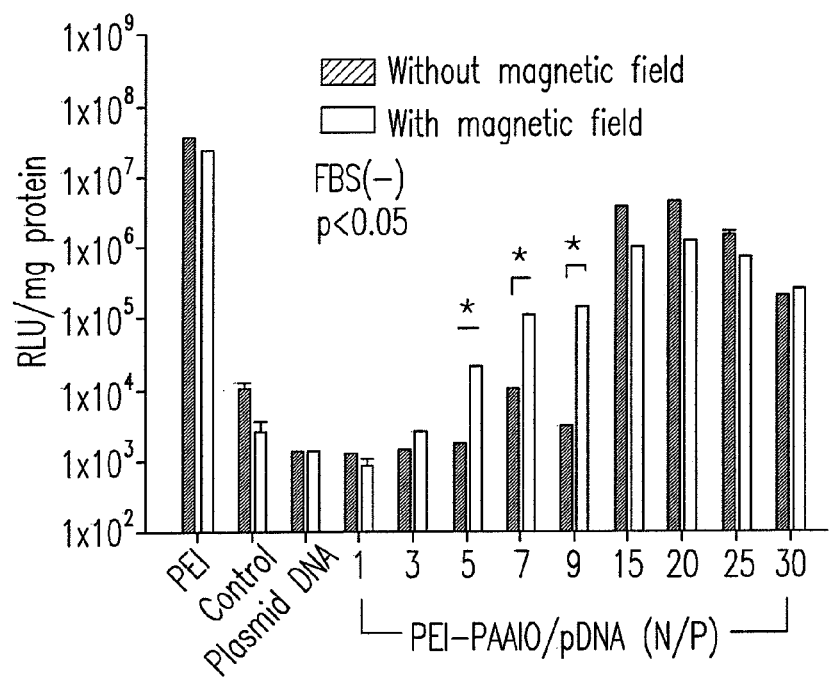
FIGS. 9(a) and 9(b) respectively illustrate the diagrams showing the luciferase activity in U87 cells exposed to PEI-PAAIO/pDNA magnetoplexes (a) without 10% FBS and (b) with 10% FBS in the absence or presence of a magnetic field for 4 hours incubation followed by 72 hours post-incubation.
Figure 9B:
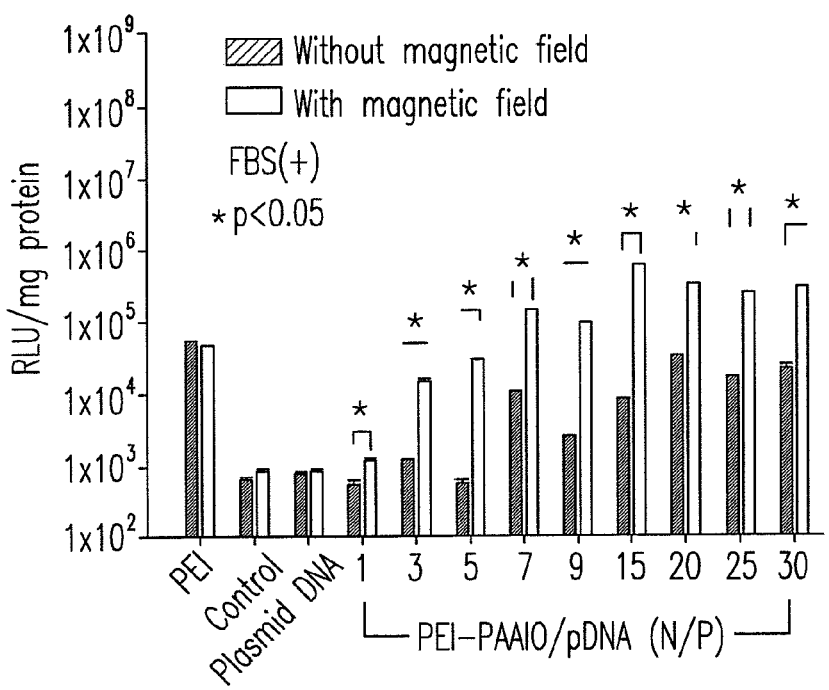
Figure 9C:
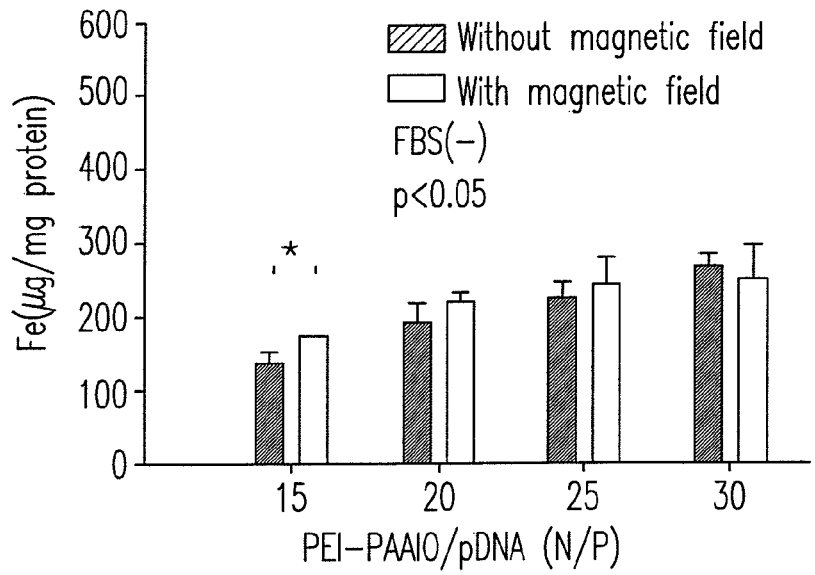
FIGS. 9(c) and 9(d) respectively illustrate the diagrams showing the U87 cell-internalized iron oxides by ICP-OES (c) without 10% FBS and (d) with 10% FBS in the absence or presence of a magnetic field for 4 hours incubation.
Figure 9D:
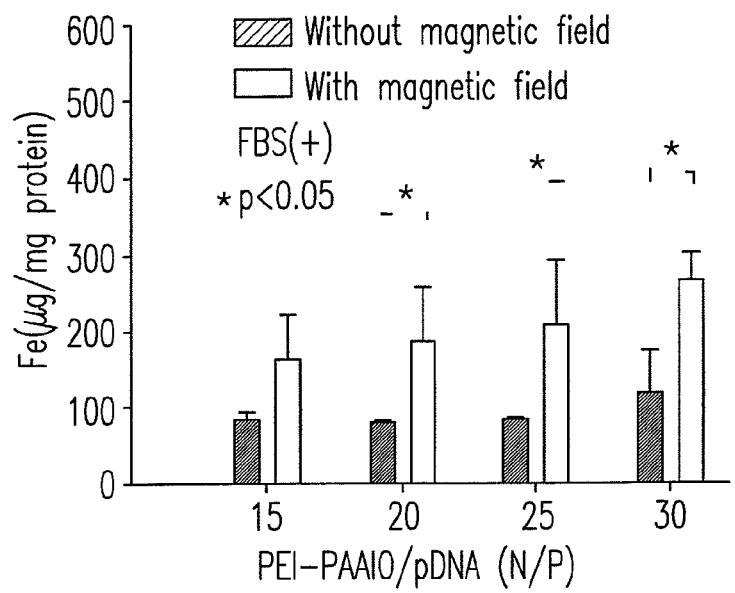

Please refer to FIGS. 9(a) and 9(b), which respectively illustrate the magnetic transfection of U87 cells (a) without 10% FBS and (b) with 10% FBS in the absence or presence of a magnetic field, and the transfection efficiency increases with an increase in the N/P ratio. In FIG. 9(b), the stimulation by the magnetic field still augments the transfection efficiency significantly. At an N/P ratio of larger than 7, the PEI-PAAIO/pDNA magnetoplexes showed higher transfection efficiency than PEI/pDNA polyplexes. Please refer to FIGS. 9(c) and 9(d), which respectively illustrate the internalized iron amount within U87 cells measured by ICP-OES (c) without FBS and (d) with FBS. Similarly, without FBS, no detectable variation in the internalized iron amount was found between with and without magnetic force. Nevertheless, in the FBS condition, U87 cells showed significant improvement in the amount of internalized iron and gene transfection in comparison with 293T cells when a magnetic field was present.

6. Conclusion

In the present invention, PAAIO was successfully coated with polyethylenimine (PEI) to form the PEI-PAAIO polyplex, and plasmid DNA then was absorbed on the PEI via electrostatic coupling. The stable and superparamagnetic PEI-PAAIO/pDNA magnetoplex was formed, which had a better transfection efficiency than PEI, and thus PEI-PAAIO could be the excellent non-viral gene vector. Under an applied magnetic field, the gene transfection efficiency of the magnetoplexes of the present invention was enhanced especially in the presence of FBS. The resistance to disruption from serum proteins is a benefit of using the PEI-PAAIO/pDNA magnetoplex for clinical applications, such as gene therapy or the powerful gene transfection tool.

Embodiments

1. A method for preparing a nanoparticle, including steps of: reacting a polyethylenimine (PEI) with a polyacrylic acid-bound iron oxide (PAAIO) to obtain a polyelectrolyte complex (PEC); and incorporating the PEC with a genetic material to form the nanoparticle.

2. The method according to embodiment 1, wherein the PAAIO is obtained by reacting a polyacrylic acid with an iron oxide.

3. The method according to at least one of embodiments 1 and 2, wherein the nanoparticle is a magnetic nanoparticle.

4. The method according to at least one of embodiments 1 to 3, wherein the PEC further includes the bound PEI, and the unbound PEI is removed by a magnetic force.

5. The method according to at least one of embodiments 1 to 4, wherein the genetic material is one selected from a group consisting of a DNA, an RNA, a complementary DNA, a micro RNA and a small interfering RNA.

6. The method according to at least one of embodiments 1 to 5, wherein the PAAIO is water soluble, and the nanoparticle has a superparamagnetic property.

7. A nanoparticle, including: a PEC including a PEI and a PAAIO configured on the PEI; and a genetic material coupled to the PEI.

8. The nanoparticle according to embodiment 7, wherein the genetic material is one selected from a group consisting of a DNA, an RNA, a complementary DNA, a micro RNA and a small interfering RNA.

9. The nanoparticle according to at least one of embodiments 7 to 8, wherein the PAAIO is water soluble.

10. The nanoparticle according to at least one of embodiments 7 to 9, wherein the PEC has a first concentration and a first volume, the genetic material has a second concentration and a second volume, the PEC and the genetic material are dissolved in a water, the first volume is equal to the second volume, and the first concentration and the second concentration have a ratio ranged from 1/1 to 1/30.

11. A nanoparticle, including: a PEC including a positive charge molecule and a magnetic particle configured on the positive charge molecule; and a genetic material coupled to the positive charge molecule.

12. The nanoparticle according to embodiment 11, wherein the positive charge molecule is one selected from a group consisting of a PEI and a PEGlyated PEI.

13. The nanoparticle according to at least one of embodiments 11 to 12, wherein the metal particle is water soluble and is one selected from a group consisting of a gold nanoparticle, a silver nanoparticle and an iron nanoparticle.

14. The nanoparticle according to at least one of embodiments 11 to 13, wherein the genetic material is one selected from a group consisting of a DNA, an RNA, a complementary DNA, a micro RNA and a small interfering RNA.

15. The nanoparticle according to at least one of embodiments 11 to 14, wherein the magnetic particle is a metal particle.

16. The nanoparticle according to at least one of embodiments 11 to 15, wherein the genetic material is electrostatically coupled to the positive charge molecule.

While the invention has been described in terms of what is presently considered to be the most practical and preferred Embodiments, it is to be understood that the invention needs not be limited to the disclosed Embodiments. On the contrary, it is intended to cover various modifications and similar arrangements included within the spirit and scope of the appended claims, which are to be accorded with the broadest interpretation so as to encompass all such modifications and similar structures.

What is claimed is:

1. A nanoparticle, comprising:
    a polyelectrolyte complex (PEC) comprising a polyacrylic acid-bound iron oxide (PAAIO) with a surface and a polyethylenimine (PEI) electrostatically decorated on the surface of the PAAIO; and
    genetic material electrostatically coupled to the PEI.

2. The nanoparticle according to claim 1, wherein the genetic material is one selected from a group consisting of a DNA, an RNA, a complementary DNA, a micro RNA and a small interfering RNA.

3. The nanoparticle according to claim 1, wherein the PAAIO is water soluble.

4. The nanoparticle according to claim 1, wherein the PEC has a first concentration and a first volume, the genetic material has a second concentration and a second volume, the PEC and the genetic material are dissolved in a water, the first volume is equal to the second volume, and the first concentration and the second concentration have a ratio ranged from 1/1 to 1/30.

* * * * *